(12) United States Patent
Jackson et al.

(10) Patent No.: US 7,888,422 B2
(45) Date of Patent: Feb. 15, 2011

(54) LONG-WEARING REMOVABLE PRESSURE SENSITIVE ADHESIVE

(75) Inventors: Kristin Jackson, Enosburg Falls, VT (US); Kenneth James Miller, II, St. Albans, VT (US)

(73) Assignee: Mylan Technologies Inc., St. Albans, VT (US)

( * ) Notice: Subject to any disclaimer, the term of this patent is extended or adjusted under 35 U.S.C. 154(b) by 999 days.

(21) Appl. No.: 11/594,224

(22) Filed: Nov. 8, 2006

(65) Prior Publication Data

US 2007/0156076 A1 Jul. 5, 2007

Related U.S. Application Data

(60) Provisional application No. 60/734,764, filed on Nov. 9, 2005.

(51) Int. Cl.
*C08L 33/06* (2006.01)
(52) U.S. Cl. .................. 524/522; 524/560; 524/561; 525/329.7; 525/329.9; 525/330.1
(58) Field of Classification Search .............. 524/522, 524/560, 561; 525/329.7, 329.9, 330.1
See application file for complete search history.

(56) References Cited

U.S. PATENT DOCUMENTS

| | | | |
|---|---|---|---|
| 4,201,211 A | 5/1980 | Chandrasekaran et al. | |
| 4,559,222 A | 12/1985 | Enscore et al. | |
| 4,588,580 A | 5/1986 | Gale et al. | |
| 4,832,953 A | 5/1989 | Campbell et al. | |
| 4,839,174 A | 6/1989 | Baker et al. | |
| 4,882,377 A | 11/1989 | Sweet et al. | |
| 4,906,463 A | 3/1990 | Cleary et al. | |
| 4,908,213 A | 3/1990 | Govil et al. | |
| 4,915,950 A | 4/1990 | Miranda et al. | |
| 4,943,435 A | 7/1990 | Baker et al. | |
| 4,997,655 A | 3/1991 | Nagy et al. | |
| 5,006,342 A | 4/1991 | Cleary et al. | |
| 5,176,915 A | 1/1993 | Hoffmann | |
| 5,186,939 A | 2/1993 | Cleary et al. | |
| 5,230,898 A | 7/1993 | Horstmann et al. | |
| 5,232,702 A | 8/1993 | Pfister et al. | |
| 5,543,231 A | 8/1996 | Kidon et al. | |
| 5,556,636 A | 9/1996 | Yano et al. | |
| 5,578,683 A * | 11/1996 | Koch et al. | 525/301 |
| 5,582,836 A | 12/1996 | Carli et al. | |
| 5,603,947 A | 2/1997 | Wong et al. | |
| 5,948,433 A | 9/1999 | Burton et al. | |
| 6,149,614 A | 11/2000 | Dunshee et al. | |
| 6,306,475 B1 | 10/2001 | Stocq et al. | |
| 6,337,086 B1 | 1/2002 | Kanios et al. | |
| 6,893,655 B2 | 5/2005 | Flanigan et al. | |
| 6,914,169 B1 | 7/2005 | Oota et al. | |
| 7,638,140 B2 | 12/2009 | Govill et al. | |
| 2002/0119187 A1 | 8/2002 | Cantor et al. | |
| 2003/0060479 A1 | 3/2003 | Brown et al. | |
| 2004/0028726 A1 | 2/2004 | Fischer et al. | |
| 2004/0202704 A1 | 10/2004 | Sharma et al. | |
| 2006/0078603 A1* | 4/2006 | Nguyen | 424/449 |
| 2006/0127464 A1* | 6/2006 | Sugawara et al. | 424/449 |
| 2007/0156076 A1 | 7/2007 | Jackson et al. | |
| 2009/0041832 A1 | 2/2009 | Govill et al. | |
| 2010/0040690 A1 | 2/2010 | Govill et al. | |

OTHER PUBLICATIONS

U.S. Appl. No. 11/899,136: File History of all prosecution documents to date, including Bibliographic Data Page and Image File Wrapper Pages from PAIR as downloaded on Aug. 29, 2010.
WO2009/032184: International Search Report dated Nov. 25, 2008 (1 page).

* cited by examiner

*Primary Examiner*—Bernard Lipman
(74) *Attorney, Agent, or Firm*—McDermott Will & Emery LLP

(57) ABSTRACT

A medical grade adhesive comprises a mixture of at least one cross-linkable pressure sensitive adhesive component and at least one non-cross-linkable pressure-sensitive adhesive component, wherein the amount of each of said components is such that the resultant adhesive can adhere to human skin for a period of up to about 7-10 days but can be removed without causing trauma to the skin.

8 Claims, No Drawings

LONG-WEARING REMOVABLE PRESSURE SENSITIVE ADHESIVE

This application claims priority from U.S. Provisional Application 60/734,764, filed Nov. 9, 2005. This prior application is incorporated herein by reference.

FIELD OF THE INVENTION

The present invention relates to pressure sensitive adhesives which can provide long-term wear on human skin but can be removed at will without causing irritation or trauma to the skin.

BACKGROUND OF THE INVENTION

Pressure sensitive adhesives are materials which adhere to a surface, such as skin, with slight pressure. Desirably, the adhesive subsequently can be released from that surface both without damaging or, if the surface is skin, causing pain to, the surface and without leaving an adhesive residue on the surface. Numerous pressure sensitive adhesives have been developed that are effective for a day or two, such as bandages to cover skin wounds or abrasions, or transdermal patches that deliver a drug or other therapeutic agent to or through the skin. In some instances, however, it is beneficial to be able to leave a pressure sensitive adhesive in place for at least several days, or perhaps a week. The development of such adhesives has been more difficult. The adhesive must bond to the skin with sufficient strength that the adhesive will remain in place for a number of days, without becoming loose or "creeping" along the skin surface, yet the composition must be removable at will without causing undo skin irritation. If the pressure sensitive adhesive is being used in a transdermal patch to deliver a therapeutic agent, the visco-elastic properties of the adhesive can be affected or compromised by the nature of the drug(s) or therapeutic agent(s), solvent(s) or excipient(s) in the composition being released to the skin. Although several long term adhesive products are commercially available, further improvements are sought.

SUMMARY OF THE INVENTION

In accordance with the present invention, a medical grade adhesive comprises a mixture of at least one cross-linkable pressure sensitive adhesive component and at least one non-cross-linkable pressure-sensitive adhesive component; wherein the amount of each of said components is such that said resultant adhesive can adhere to human skin for a period of up to about 7-10 days but can be removed without causing trauma to the skin. Desirably, both adhesives are acrylic adhesives.

In a preferred embodiment, the cross-linkable component and the non-cross-linkable component are provided in a weight:weight ratio of about 60:40 to about 40:60. More preferably, the components are provided in a weight:weight ratio of about 50:50.

DETAILED DESCRIPTION OF THE INVENTION

It has been discovered that by mixing together at least one cross-linkable adhesive with at least one non-cross-linkable adhesive within certain weight:weight ratios, one can make an adhesive which is highly suitable for long-term wear on human skin but also can be removed when desired without causing trauma to the skin. As used herein, "trauma" is defined to mean undue irritation or damage to skin.

Cross-linkable adhesives useful in making the adhesive composition of the present invention include medical grade acrylic cross-linkable adhesives. As used herein, "cross-linkable adhesive" refers to an adhesive provided as a solvent-based solution that contains a cross-linking agent. As provided, the adhesive is uncross-linked; when the solution is dried to remove the solvent, the cross-linker is activated and the cross-linking of the adhesive occurs. Suitable acrylic adhesives include acrylate-vinylacetate self-curing pressure sensitive adhesives, such as Duro-Tak® 387-2516/87-2516.

Prior to drying, the cross-linkable acrylic adhesive is mixed with a second, non-cross-linkable acrylic adhesive. As used herein, a "non-cross-linkable adhesive" refers to an adhesive provided as a solvent-based solution that does not contain a cross-linking agent. Preferably the solution of non-cross-linkable adhesive comprises the same polymer as provided in the solution of the cross-linkable adhesive. Thus, if the cross-linkable adhesive comprises Duro-Tak® 387-2516/87-2516, the non-cross-linkable adhesive comprises Duro-Tak® 387-2287/87-2287.

In accordance with the present invention, the adhesive solution of the non-cross-linkable adhesive can be mixed with a solution of the cross-linkable adhesive and cross-linking agent and then dried such that the resultant product is a combination of the cross-linkable adhesive and the non-cross-linkable adhesive. By blending the two solvent-based adhesive solutions prior to drying, the cross-linker in the one solution, in essence, is diluted, such that the final product is a combination of cross-linked and non-cross-linked adhesives, with a blend of the properties of each adhesive taken independently. The particular properties of the product will depend on the ratio of cross-linkable adhesive to non-cross-linkable adhesive. A variety of ratios can be used to make an adhesive product having the balance of properties (duration of wear vs. removability) desired for this invention; generally, the ratio of cross-linkable adhesive to non-cross-linkable adhesive is within the range of 60:40 to 40:60 weight:weight. An especially preferred ratio is 50:50 weight:weight.

The cross-linked component of the final adhesive product provides mechanical strength to the composition such that it has a consistent bond and is not liable to slip or "creep" during wear (i.e., it stays where placed on the skin). The non-cross-linked component enhances wetting of the skin when the adhesive composition is applied so as to promote rapid bonding of the composition to the skin. By balancing the ratio of cross-linkable adhesive to non-cross-linkable adhesive, one can prepare a composition which will wear more consistently only as long as needed or desired. The bond between the adhesive and the skin is engineered so that the adhesive is effectively bonded for the entire desired wear period but is easily removable at the end of the treatment period while leaving minimal to no adhesive residue on the surface of the skin. Typically, for example, adhesive compositions made with the Duro-Tak® adhesives referenced above in a weight:weight ratio of 60:40 to 40:60 can be worn for a period of up to about 7-10 days and then easily removed.

The adhesives of this invention can be used as a means of adhering an associated drug delivery system or a drug-containing delivery matrix to the skin for transdermal delivery of the drug. The adhesives also can be used as a means for adhering a wound dressing, prosthesis, colostomy bag, electrode, diagnostic device, or active delivery device (e.g., iontophoresis, electrophoresis, electroporation, RF-ablation, micro-needles, phonophoresis, etc.) to skin for extended periods.

In one preferred embodiment, the adhesive is used in combination with a drug-containing reservoir or matrix for transdermal drug delivery. Drug reservoirs typically comprise a drug, carrier, and any additional desired components within synthetic, polymeric films and/or membranes. The drug diffuses through the film or membrane at a controlled rate to the skin. Matrix systems typically comprise a polymeric matrix consisting of a single phase mixture (solution) or two-phase mixture (suspension) of a drug of interest. The drug is released by diffusion through the matrix. In a third possible embodiment, there is a combined reservoir and matrix system; the drug is released by a combination of diffusion through a polymeric solution and diffusion across a polymeric membrane. All three types of delivery systems are well-known in the art, and a wide variety of reservoirs and matrix systems can be used with the adhesives of the present invention.

As used herein, the term "drug" is intended to have its broadest interpretation as including any therapeutically, prophylactically and/or pharmacologically or physiologically beneficial active substance, or a mixture thereof, which is delivered to a living being to produce a desired, beneficial effect. More specifically, any drug which can produce a pharmacological response, localized or systemic, whether therapeutic, diagnostic, or prophylactic in nature, is within the contemplation of the present invention. Also included within the scope of the invention are bioactive agents, such as insect repellants, sun screens, cosmetic agents, etc. The drug can be provided in an amount sufficient to cure, diagnose, or treat a disease or condition. This definition includes, but is not limited to:

1. cardiovascular drugs, such as nitroglycerin, propranolol, isosorbide dinitrate, isosorbide mononitrates, diltiazem, nifedipine, procainamide, clonidine and others,
2. androgenic steroids, such as testosterone, methyltestosterone and fluoxymesterone,
3. estrogens, such as conjugated estrogens, esterified estrogens, etropipate, 17-β estradiol, 17-β estradiol valerate, equilin, mestranol, estrone, estriol and diethylstilbestrol,
4. progestational agents, such as progesterone, 19-norprogesterone, norethindrone, norethindrone acetate, melengestrol chloradinone, ethisterone, medroxyprogesterone acetate, hydroxyprogesterone caproate, norethynodrel, dimethisterone, ethinylestrenol, norgestrel, megestrolacetate, and ethinodiol diacetate,
5. drugs which act on the central nervous system, including sedatives, hypnotics, analgesics, anesthetics, and antianxiety agents; such as opiates, opioids and the like; including chloral hydrate, benzodiazepines, naloxone, haloperidol, pentobarbitol, phenobarbitol, secobarbital, codeine, fentanyl, fentanyl analogs and nicotine,
6. nutritional agents, including vitamins, essential amino acids and essential fats,
7. anti-inflammatory agents, including hydrocortisone, cortisone, dexamethasone, prednisolone, prednisone, halcinonide, methylprednisolone, flurocortisone, corticosterone, paramethasone, ibuprofen, naproxen, fenoprofen, fenbufen, indoprofen, salicylic acid derivatives, methyl salicylate, sulindac, mefenamic acid, piroxicam, indonisilone and tolmetin,
8. antihistamines, such as diphenhydramine, triprolidine, chlorcyclizine, promethazine, cyclizine, chlorprenaline, terrenadine and chlorpheniramine,
9. miotics, such as pilocarpine,
10. dermatological agents, such as vitamins A and E or fruit acids,
11. anti-spamodics, including atropine, methantheline, papverine, cinnmedrine, methscopolamine and scopolamine,
12. anti-depressants, such as isocaboxazid, phenelzine, imipramine, amitrptyline, trimepramine, dozepin, desipramine, nortriptyline, protriptyline, amoxapine, maprotiline and selegiline,
13. anti-cancer drugs,
14. anti-diabetics, such as insulin and rosiglitazone,
15. anti-estrogens or hormone agents, including tamoxifen or HCG,
16. anti-infectives, including antibiotics, anti-bacterials and anti-virals, such as tetracycline, chloramphenicol, sulfacetamide, sulfadiazine, sulfamerazine, sulfoxazole, idoxuridine, and erythromycin,
17. anti-allergenics, such as antazoline, metapyrilene, and pyrilamine,
18. anti-pyretics, including aspirin and salicylamide,
19. anti-migraine agents, including dihydroergotamine, pizotyline and sumatriptan,
20. tranquilizers, including reserpine, chlorpromazine, and antianxiety benzodiazepines,
21. anti-psychotic agents, including haloperidol loxapine, molindone, thiothixene, pimozide, risperidone, quetiapine fumarate, olanzapine, and/phenothiazine derivatives,
22. anti-smoking agents, and
23. local anesthetic agents, including lidocaine, dibucaine and benzocaine.

Other drugs suitable for delivery using a transdermal system can be readily determined by persons of ordinary skill in the art. In addition, pharmacologically acceptable derivatives of the drugs, such as ethers, esters, amides, acetals, salts and the like, which are suitable for transdermal administration can be used.

Compositions comprising a drug or other therapeutic agent-containing reservoir and/or a matrix and a pressure sensitive adhesive in accordance with this invention typically also comprise a backing and a release liner, each of which can comprise materials conventionally used in transdermal drug delivery compositions. The backing is attached to one face of the reservoir or matrix; the release liner releasably covers the adhesive formulation attached to a second, opposing face of the reservoir or matrix.

The backing can comprise any material conventionally used as such in transdermal patch compositions. The material chosen for the backing is one which is flexible and impermeable to the drug, and, if desired, can be colored or labeled. The backing provides support and a protective covering for the dosage unit. Suitable backing materials include those known in the art for use with pressure sensitive adhesives. For example, the backing can comprise a polyolefin, polyether, multi-layer EVA film, polyester, polyurethane or combination thereof. Preferred backings include MEDIFLEX® 1000, a polyolefin manufactured by Mylan Technologies, Inc. or Volara® 6 EO 0.031 SK foam, a cross-linked fine-celled foam manufactured by Votek, Inc.

Release liners are used to cover the surface of the pressure-sensitive adhesive during storage. If the adhesive is used in combination with a drug delivery system or matrix the release liner can prevent evaporative loss of one or more components of the drug delivery system or matrix that may have migrated into the adhesive layer. The release liner is removed and discarded from the composition to expose the adhesive which will be applied to the patient's skin. Suitable release liners include those known in the art for use with pressure sensitive adhesive composition. For example, the release liner can comprise a fluorosilicone coated polyester, silicone coated polyester or a UV cured, silicone-coated polyester. Preferred release liners include MEDIRELEASE® 2500, MEDIRELEASE® 2249 and MEDIRELEASE® 2226, each manufactured by Mylan Technologies, Inc., Clearsil® release liner UV5A manufactured by CPFilms, Inc. or Scotchpak™ 1022, manufactured by 3M Pharmaceuticals/D.D.S. The release liner, however, can comprise other materials, including paper or paper-containing layers or laminates, various thermoplastics, polyester films, foil liners, and the like.

Non-adhesive components can be included in the adhesive composition, including preservatives, antioxidants and chelating agents. Suitable examples of such compounds include butylated hydroxyanisole (BHA), butylated hydroxytoluene (BHT), sodium metabisulfate, a tocopherol, maleic acid, ethylenediaminetetraacetic acid (EDTA), cysteine hydrochloride, colloidal silicone dioxide and metal oxides (ZnO, $TiO_2$, etc.).

The adhesive composition further can include polymeric matrix-forming materials which can facilitate the curing of the adhesive, a thickener to adjust the viscosity of the mixture, or a stabilizer to prevent degradation upon exposure to light or heat, such as polyvinylpyrrolidone (PVP).

The choice, effects and suitable amounts of these excipients are in keeping with their use in conventional formulations and those of ordinary skill in the art can determine suitable excipients through routine experimentation or selection.

The present invention is further described in the following examples, which are provided for illustration and are not intended to be limiting.

EXAMPLES

The following examples describe two different types of systems:

1) a double-disk system in which, typically, a smaller patch (inner disk) comprised of a backing film and an adhesive formulation is centered and attached to a larger adhesive patch by placing the backing of the smaller disk onto the adhesive of the larger disk. The adhesive side of the double disk then is covered with a protective release liner. In some of the examples below, a double-disk system is described in which the adhesive of the inner disk alone previously has been determined to be insufficient for the wear period. In these situations the double disk comprises a smaller inner disk typically containing the drug delivery formulation and an outer (larger) disk that ensures adhesion for the wear period. The focus of this invention and the following examples is the outer disk. The composition of the inner disks can vary widely and is not necessarily the focus of the examples.

2) a single disk or double disk system supplied with a separate (i.e., unattached) overlay known as a "rescue" overlay. The "rescue" overlay typically is provided with the systems for medical or cost reasons and provides the patient a supplemental or alternate means of ensuring adhesion of the system to the skin in the event of disadhesion of the single disk or double disk system over the course of the wear period.

It should be noted that outer disk dimensions in a double disk typically are chosen to provide at least a 0.5 cm annulus around the inner disk. "Rescue" overlay dimensions typically are chosen to provide at least a 1.0 cm annulus around the single disk or double disk system.

Example 1

A 50/50 blend (w/w by solids) mixture of Duro-Tak® 387-2516/87-2516 and Duro-Tak® 387-2287/87-2287 was made by weighing 120.48 g of Duro-Tak® 387-2516/87-2516 and 99.66 g of Duro-Tak® 387-2287/87-2287 into the same jar. The wet blend was mixed with the laboratory propeller mixer for 3 minutes to create a uniform mixture. The blend was rolled on a jar roller to de-gas.

For the coating procedure, the wet blend was coated onto MEDIRELEASE® 2249 release liner to achieve a ~95 gsm dry coat weight. The coating was dried for 1 minute at room temperature in the laboratory hood, 5 minutes at 55° C. and 5 minutes at 85° C. The dried coating was laminated to Volara® 6 EO 0.031 SK foam, a cross-linked fine-celled foam used herein as a backing. This was labeled as lot # 257p50A and was used to make an outer disk laminate known as MEDIDERM® 3505.

Lot #257p50A as described above was die cut at 33.4 $cm^2$ as an outer disk. An inner disk laminate comprised of a pressure sensitive adhesive, excipients and enhancers, identified as lot # R&D-I581, was die cut at 24 $cm^2$ (manufactured by Mylan Technologies, Inc.). This lot was made in accordance with a standard Mylan Technologies, Inc., batch record, utilizing an adhesive mixing process followed by knife-over-roll coating and drying in a heated drying tunnel to remove the solvent.

Double disk assembly procedure was as follows: double-disk prototypes were assembled in the laboratory by peeling the release liner off the outer disk and placing the inner disk (backing side toward the outer disk adhesive) in the center of the outer disk. The release liner was removed from the inner disk and a new MEDIRELEASE® 2249 release liner was placed, release side toward the adhesive, on top of the double disk system.

A directional (screening) study tested the double disk prototype (with the adhesive mixture outer disk) adhesion over 7 full days on the abdomens of ten volunteers. An analogous system with only a Duro-Tak® 387-2516/87-2516 outer disk was used as a control. The results of the study showed that the outer disk adhesive mixture prototype adhered for 7 days on more volunteers than the prototype system containing only the Duro-Tak® 387-2516 outer disk. Also, the prototype with the outer disk adhesive mixture had one less fall-off after 7 days. This study provided direction for development and further testing of the 50/50 mixture of Duro-Tak® 387-2516/87-2516 and Duro-Tak® 387-2287/87-2287 outer disk prototype known as MEDIDERM® 3505.

Example 2

An adhesive blend was created by mixing 101.9 kg of Duro-Tak® 87-2516 self-crosslinking acrylic adhesive solution and 54.9 kg of Duro-Tak® 87-2287 non-crosslinking acrylic adhesive solution. Both adhesives were manufactured by National Starch and Chemical Company and contained 41.2% and 51% solids, respectively.

The adhesive solutions were blended in a manufacturing mixer for 45 minutes and then transferred to a steel 55 gallon drum for storage prior to coating. The adhesive blend was continuously coated onto MEDIRELEASE® 2226 release liner (manufactured by Mylan Technologies, Inc.) via knife-over-roll coating method. The solvent was removed by passing the wet coating through a 2-zone drying tunnel at 6 feet per minute before being laminated to Volara® 6 EO 0.031SK Foam manufactured by Voltek Inc. Zone 1 of the drying tunnel was held at 200° F. Zone 2 of the drying tunnel was held at 240° F. Each zone was 15 feet long so the residence time in each zone was approximately 2.5 minutes or 5 minutes from coating to lamination. The resulting dry adhesive film, MEDIDERM® 3506, contained 60% Duro-Tak® 87-2516 and 40% Duro-Tak® 87-2287.

A coated laminate comprised of a pressure sensitive adhesive, drug excipients and enhancer, was manufactured and used as the inner disk.

Double-disk Assembly Procedure: The MEDIDERM® adhesive laminate described above was used as the outer (larger) disk in a double-disk transdermal system on a commercial die cutting machine. This continuous process involved die cutting the inner disk to 6.67 cm$^2$, removing the surrounding waste material and leaving a continuous release liner intact. The release liner for the outer disk material was removed and discarded. The exposed adhesive was laminated to the backing side of the die cut inner disk patches on release liner. The resulting laminate then was die cut to 15 cm$^2$ (centered on the smaller 6.67 cm$^2$ patches) and the surrounding waste material removed, leaving the release liner intact. The continuous role of die cut double-disk patches on release liner was rewound and stored prior to final packaging.

A clinical study was performed with one hundred fifty (150) healthy adult volunteers to evaluate the adhesion and irritation qualities of the resulting transdermal system. The adhesion quality was assessed daily and all 150 subjects enrolled into the study were included in the adhesion analysis. One hundred twenty-four subjects were included in the irritation analysis.

The transdermal system was applied to a clean, dry area of skin on the upper outer right or left arm, according to the randomization scheme, and was worn for a maximum of 7 days. There were no food or water restrictions on the volunteers in this study. The adhesion of the transdermal system to the skin was assessed at 24, 48, 72, 96, 120, 144, and 168 hours post patch application. Adhesion assessment was based upon a pre-determined rating scale that ranged from 0-4, where 0 referred to the patch being at least 90% adhered to the skin and 4 indicated that the patch had detached (patch completely off the skin). If the transdermal system began to lift off during the 7-day application period (an adhesion score greater than 0), a rescue overlay (not the same type of "rescue" overlay of this invention) was centered and applied directly over the patch.

If the transdermal system, whether it had a "rescue" overlay or the double disk system only, became detached over the seven days of application, the treatment site was not considered valid for irritation evaluation. skin irritation was assessed thirty (30) minutes after patch The MEDIDERM® 3506 system wore very well, as shown in Table 1 and by the relatively low number of rescue overlays required (only seven were applied out of 150 subject tested (less than 5%).

The system produced very little irritation after one full week on the skin with a mean irritation score of 1.94, indicating barely perceptible to minor redness of the scoring for the irritation test is described below, following Table 1.

TABLE 1

MEAN TRANSDERMAL SYSTEM ADHESION SCORE IN ONE HUNDRED FIFTY (150) HEALTHY ADULT VOLUNTEERS FOLLOWING A SINGLE PATCH APPLICATION WORN FOR THE 7 DAYS

| Days After System Application | Mean Adhesion Score* | Rescue Overlays Used (%) |
|---|---|---|
| 1 | 0.00 | 0 |
| 2 | 0.00 | 0 |
| 3 | 0.03 | 0 |
| 4 | 0.03 | 3 (2.00) |
| 5 | 0.06 | 4 (2.67) |
| 6 | 0.10 | 5 (3.33) |
| 7 | 0.09 | 7 (4.67) |

*Adhesion Score
0: ≧90% adhered (essentially no lift off from the skin)
1: ≧75% to <90% adhered (some edges only lifting off the skin)
2: ≧50% to <75% adhered (less than half the system lifting off the skin)
3: <50% adhered but not detached (more than half lifting off the skin)
4: patch detached (patch completely off the skin)

Example 3

An adhesive blend was created by mixing 74.1 kg of Duro-Tak® 87-2516 self-crosslinking acrylic adhesive solution and 60.9 kg of Duro-Tak® 87-2287 non-crosslinking acrylic adhesive solution. Both adhesives were manufactured by National Starch and Chemical Co and contained 41.5% and 50.0% solids, respectively. The adhesive solutions were blended in a manufacturing mixer for 20 minutes prior to coating.

The adhesive blend was continuously coated onto MEDIRELEASE® 2226 release liner (manufactured by Mylan Technologies Inc.) via knife-over-roll coating method. The solvent was removed by passing the wet coating through a 2-zone drying tunnel at 6 feet per minute before being laminated to Volara® 6 EO 0.031SK Foam manufactured by Voltek Inc. Zone 1 of the drying tunnel was held at 200° F. and Zone 2 was held at 240° F. Each zone was 15 feet long so the residence time in each zone was approximately 2.5 minutes or 5 minutes from coating to lamination. The resulting dry adhesive film contained 50% Duro-Tak® 87-2516 and 50% Duro-Tak® 87-2287.

The double-disk assembly procedure was conceptually the same as for Example 1 but used the MEDIDERM® 3505 described above as an outer disk. The inner disk laminate was made in the laboratory and comprised a pressure sensitive adhesive, excipients and enhancers. The double-disk dimensions were 20 cm$^2$ (inner) and 33.4 cm$^2$ (outer).

In addition, a 54 cm$^2$ "rescue" overlay was manufactured from the same MEDIDERM® 3505 adhesive laminate.

The placebo prototype system was evaluated for skin adhesion using the same 0-4 scale as Example 2; however, adhesion was evaluated only upon system removal (168 hours post patch application). Irritation was not necessarily scored unless notable as determined by the volunteers.

A directional (screening) study on fifteen volunteers tested two double-disk patches (one on each arm), one applied alone and the other with an immediately applied "rescue" overlay patch over the double-disk patch. A "rescue" overlay patch then was applied over the lone double-disk patch only if the double-disk patch began to lift off the skin. In the group without a "rescue" overlay applied immediately, only one of the 15 volunteers required a "rescue" overlay.

Fourteen of 15 patches in each group remained fully adhered to the skin (no lift) for 7 full days. Two of the 15 volunteers reported minor irritation after removing the patches. This study provided direction for development and further testing of the MEDIDERM® 3505.

Example 4

The same MEDIDERM® 3505 laminate produced in Example 3 was used to make placebo double-disk systems as described in the double-disk assembly procedure of Example 2 except that the patch dimensions were 31 cm² (inner) and 42 cm² (outer). The inner disk was comprised of a pressure sensitive adhesive, excipients and enhancers.

A different MEDIDERM® laminate, MEDIDERM® 3500 (made with only Duro-Tak® 87-2516 adhesive) on Volara® 6 EO 0.031SK Foam was used to make double-disk control systems following the same procedure described in the preceding paragraph.

A clinical study was performed with forty (40) healthy female adult volunteers to evaluate the adhesion quality and primary dermal irritation of the double-disk systems following a single application of 7 days (168 hours).

Each subject wore four patches for the 7-day study period (one of each MEDIDERM® type on the abdomen and one of each on the buttocks). Each subject was randomized as to the placement of each MEDIDERM® type patch on the upper quadrant of the right and left buttock and on the right and left abdomen. Adhesion was evaluated daily for the 7-day study by the same study monitor based upon a pre-determined rating scale that ranged from 0-4, where 0 referred to the patch being >90% adhered to the skin and 4 indicated the patch detached (patch completely off the skin). All irritation assessments were made after patch removal by the same person who was blinded as to the treatment assignments.

Thirty-nine subjects completed the study. Each subject wore two patches per prototype (one patch on each wear site-buttocks or abdomen) for a total of four patches per subject. The observations were pooled, yielding 78 observations per prototype.

Table 2 shows that the adhesion of the mixed adhesive system (MEDIDERM® 3505) was significantly better ($p \leq 0.05$) than that of the pure Duro-Tak® 87-2516 system (MEDIDERM® 3500) at every time point except the first (24 hours, $\alpha = 0.08$). The mean irritation score for both systems was 0.46 immediately after removal on day 7. This mean score is between 0 (no reaction) and 0.5 (faint redness). After 30 minutes, both mean irritation scores dropped below 0.30.

| | Mean Adhesion Score* | | Patches Fallen Off | |
|---|---|---|---|---|
| Days After System Application | 50% w/w Duro-Tak® 87-2516 50% w/w Duro-Tak® 87-2287 | 100% Duro-Tak® 87-2516 | 50% w/w Duro-Tak® 87-2516 50% w/w Duro-Tak® 87-2287 | 100% Duro-Tak® 87-2516 |
| 1 | 0.06 | 0.15 | 0% | 0% |
| 2 | 0.17 | 0.79 | 2.56% | 0% |
| 3 | 0.24 | 0.90 | 2.56% | 1.28% |
| 4 | 0.42 | 1.05 | 2.56% | 2.56% |
| 5 | 0.53 | 1.08 | 2.56% | 2.56% |
| 6 | 0.58 | 1.31 | 2.56% | 3.85% |
| 7 | 0.62 | 1.45 | 2.56% | 5.13% |

*Adhesion Score
0: >90% adhered (essentially no lift off from the skin)
1: ≧75% to <90% adhered (some edges only lifting off the skin)

| | Mean Adhesion Score* | | Patches Fallen Off | |
|---|---|---|---|---|
| Days After System Application | 50% w/w Duro-Tak® 87-2516 50% w/w Duro-Tak® 87-2287 | 100% Duro-Tak® 87-2516 | 50% w/w Duro-Tak® 87-2516 50% w/w Duro-Tak® 87-2287 | 100% Duro-Tak® 87-2516 |

2: ≧50% to <75% adhered (less than half the system lifting off the skin)
3: <50% adhered but not detached (more than half lifting off the skin)
4: patch detached (patch completely off the skin)

Example 5

A 50/50 mixture (w/w by solids) of Duro-Tak® 87-2516 and Duro-Tak® 87-2287 was made by weighing 60.39 g of Duro-Tak® 87-2516 and 48.73 g of Duro-Tak® 87-2287 into a jar. The blending, coating, drying, minating and double-disk construction processes were conceptually the same as in Example 1 except the backing used for the outer disk was a clear polyolefin film (MEDIFLEX® 1000) manufactured by Mylan Technologies Inc. The resulting outer disk dry adhesive film, MEDIDERM® 3807, contained 50% Duro-Tak® 87-2516 and 50% Duro-Tak® 87-2287.

The double-disk assembly procedure was conceptually the same as for Example 1. MEDIDERM® 3807 was die cut and used as the outer disk adhesive laminate at 12.6 cm². Inner disk laminate was made in the laboratory and was comprised of a pressure sensitive adhesive or a mixture of two pressure sensitive adhesives. The inner disk laminate was die cut to 6.25 cm².

Double-disk assembly procedure was as follows: double-disk prototypes were assembled in the laboratory by peeling the release liner off the outer disk and placing the inner disk (backing side toward the outer disk adhesive) in the center of the outer disk. The release liner was removed from the inner disk and a new Scotchpak™ 1022 release liner was placed, release side toward the adhesive, on top of the double disk system.

A directional (screening) study tested a pooled group of two double-disk MEDIDERM® 3807 systems with similar inner disk adhesives versus a pooled group of two monolithic (inner disk only) equivalents. Both of the double-disks were tested for skin adhesion over 7 full days on the upper arms of thirteen volunteers versus their two monolithic (inner disk only) equivalents. Since the double disk systems were similar compositions, the data were pooled for the double-disks, yielding 26 observations, the data also were pooled for the monolithic equivalent systems, yielding another 26 parallel observations.

The study illustrated that the MEDIDERM® 3807 (50% Duro-Tak$^7$87-2516 and 50% Duro-Tak$^7$87-2287 outer disk on MEDIFLEX® 1000) improves the adhesion over a monolithic formulation (inner disk only). All 26 observations on the MEDIDERM® 3807 double-disk systems illustrated the double disks remained completely attached after 7 days. For the monolithic (inner disk only) systems, 8 of the 26 observations were fall offs.

Example 6

A 50/50 mixture (w/w by solids) of Duro-Tak® 87-2516 and Duro-Tak® 87-2287 was made by weighing 301.93 g of Duro-Tak® 87-2516 and 250.00 g of Duro-Tak® 87-2287 into a jar. The blending, coating, drying, aminating and double-disk construction processes were conceptually the same as in Example 1. The backing used for the outer disk was a clear polyolefin film (MEDIFLEX® 1000) manufactured by Mylan Technologies Inc. The resulting outer disk dry adhesive film, MEDIDERM® 3807, contained 50% Duro-Tak® 87-2516 and 50% Duro-Tak® 87-2287.

The double-disk assembly procedure was conceptually the same as for Example 5. An inner disk laminate was made in the laboratory and was comprised of a mixture of pressure sensitive adhesives. The double-disk dimensions were 6.25 cm$^2$ (inner) and 12.6 cm$^2$ (outer).

In addition, a 31.29 cm$^2$ "rescue" overlay was die cut from a MEDIDERM® 3505 adhesive laminate (50% Duro-Tak® 87-2516 and 50% Duro-Tak® 87-2287 on Volara® 6 EO 0.031SK Foam).

To determine the effectiveness of a "rescue" overlay, a directional (screening) study evaluated adhesion upon system removal (168 hours post patch application). Twelve volunteers applied two double disk patches (one of each arm) and immediately applied a "rescue" overlay patch over one double-disk system. A rescue overlay patch was applied over the other double-disk patch only if it began to lift off the skin. Irritation was not necessarily scored unless notable as determined by the volunteers.

Eleven out of 12 systems in the group with the "rescue" overlay applied immediately remained fully adhered (no lift) for the full 7 days of the trial.

Three of the 12 volunteers required a "rescue" overlay (although 1 patch still fell off) for the group of double-disks applied without the initial application of a "rescue" overlay. Eight of the 12 systems without a "rescue" overlay applied remained fully adhered (no lift) for the full 7 days. One patch of the 12 without a rescue overlay was removed early by the volunteer.

This study showed that the MEDIDERM® 3505 "rescue" overlay can maintain adhesion for the full 7 day wear period whether applied initially or as needed when the double disk system begins to lift.

Example 7

The same MEDIDERM® 3807 laminate described in Example 6, containing 50% Duro-Tak® 87-2516 and 50% Duro-Tak® 87-2287, was used in the following example.

The double-disk assembly procedure was conceptually the same as for Example 5. An inner disk laminate was made in the laboratory and contained a mixture of pressure sensitive adhesives. The double-disk dimensions were 25.00 cm$^2$ (inner) and 36.24 cm$^2$ (outer).

In addition, a 63.00 cm$^2$ "rescue" overlay was die cut from a MEDIDERM® 3505 adhesive laminate (50% Duro-Tak® 87-2516 and 50% Duro-Tak® 87-2287 on Volara® 6 EO 0.031SK Foam).

To determine the effectiveness of a "rescue" overlay, a directional (screening) study evaluated adhesion upon system removal (168 hours post patch application). Twelve volunteers applied two double-disk patches (one on each arm) and immediately applied a "rescue" overlay over one double disk system. A "rescue" overlay was applied over the other double-disk only if it began to lift off the skin. Irritation was not necessarily scored unless notable as determined by the volunteers.

Four volunteers removed both patches prior to the end of the 7 day study due to excessive itching, sunburn or a small bruise (the latter two causes for voluntary discontinuation are assumed unrelated to the study).

Five out of the 8 remaining attached systems in the group with the "rescue" overlay applied immediately remained >90% adhered for the full 7 days.

Three of the 8 volunteers required a "rescue" overlay (although 1 patch still fell off) for the group of double-disks applied without a "rescue" overlay initially.

This study showed that the MEDIDERM® 3505 "rescue" overlay can maintain adhesion for the full 7 day wear period whether applied initially on day 0 or as needed when the double disk system begins to lift. However, the larger patch size may have led to the higher adhesion scores in this screening study compared to Example 6.

The invention claimed is:

1. A pressure sensitive adhesive formulation comprising a mixture of at least one self-cross-linkable acrylic adhesive component and at least one non-self-cross-linkable acrylic adhesive component; said at least one self-cross-linkable acrylic adhesive and said at least one non-self-cross-linkable adhesive provided in such relative amounts that said adhesive formulation can adhere to human skin for a period of about 7-10 days but can be removed without causing trauma to the skin.

2. The pressure sensitive adhesive formulation of claim 1, wherein said self-cross-linkable adhesive is provided as a solvent-based adhesive solution that contains a cross-linking agent.

3. The pressure sensitive adhesive formulation of claim 2, wherein said non-self-cross-linkable adhesive is provided as a solvent-based adhesive solution that does not contain a cross-linking agent.

4. The pressure sensitive adhesive formulation of claim 3, wherein said self-cross-linkable adhesive solution and said non-self-cross-linkable adhesive solution comprise the same acrylic polymer.

5. The pressure sensitive adhesive formulation of claim 1, wherein said self-cross-linkable adhesive and said non-self-cross-linkable adhesive are provided within about a 60:40 to about 40:60 weight:weight ratio (dry solids).

6. The pressure sensitive adhesive formulation of claim 5, wherein said self-cross-linkable adhesive and said non-self-cross-linkable adhesive are provided in about a 50:50 weight:weight ratio (dry solids).

7. The pressure sensitive adhesive formulation of claim 1, wherein said adhesive formulation can adhere to human skin for a period of about 7 days.

8. The pressure sensitive adhesive formulation of claim 1, wherein said adhesive formulation can adhere to human skin for a period of about 10 days.

* * * * *